US012678334B2

(12) United States Patent
Kårekull et al.

(10) Patent No.: US 12,678,334 B2
(45) Date of Patent: Jul. 14, 2026

(54) HEARING PROTECTOR WITH SPRING ELEMENT AND A CARRIER

(71) Applicant: 3M INNOVATIVE PROPERTIES COMPANY, St. Paul, MN (US)

(72) Inventors: Oscar J. Kårekull, Huskvarna (SE); Tim S. Hjertberg, Jönköping (SE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 267 days.

(21) Appl. No.: 18/552,921

(22) PCT Filed: Mar. 25, 2022

(86) PCT No.: PCT/IB2022/052753
§ 371 (c)(1),
(2) Date: Sep. 28, 2023

(87) PCT Pub. No.: WO2022/208261
PCT Pub. Date: Oct. 6, 2022

(65) Prior Publication Data
US 2024/0189152 A1     Jun. 13, 2024

(30) Foreign Application Priority Data
Apr. 1, 2021    (EP) ..................................... 21166716

(51) Int. Cl.
*A61F 11/14*            (2006.01)
(52) U.S. Cl.
CPC ................................... *A61F 11/145* (2022.01)
(58) Field of Classification Search
CPC .................... A61F 11/14; A61F 11/145; A61F 2230/0065; A61F 11/08; A61F 11/12;
(Continued)

(56) References Cited

U.S. PATENT DOCUMENTS 3,306,991 A  *  2/1967  Wood ................... H04R 5/0335
                                                        381/322
3,506,981 A      4/1970  Stewart et al.
(Continued)

FOREIGN PATENT DOCUMENTS

CN        201147414  Y     11/2008
CN        203943806  U     11/2014
(Continued)

OTHER PUBLICATIONS

International Search Report for PCT International Application No. PCT/IB2022/052753, mailed on Jun. 13, 2022, 3 pages.

*Primary Examiner* — Lun-See Lao
(74) *Attorney, Agent, or Firm* — Katherine M. Scholz

(57) ABSTRACT

In a first aspect, the present disclosure relates to a hearing protector 10 including two earmuffs 12A, 12B each with a cushion 16A, 16B, a cup 14A, 14B and a carrier 24A, 24B. The hearing protector 10 further includes a headband 18, or alternatively two helmet mounts, with two earmuff attachment means 22A, 22B as well as a spring element 30A, 30B. The carrier 24A, 24B and the cushion 16A, 16B form a first mass-spring system. The cup 14A, 14B and the spring element 30A, 30B form a second mass spring system. The spring element 30A, 30B is configured and arranged such that the cup 14A, 14B and the carrier 24A, 24B are mechanically decoupled from each other. The advantage of such a hearing protector 10 is that the hearing protector 10 can be designed such that the aspects of comfort and noise attenuation can be addressed more independent of each other. Also, the force or pressure applied to the carrier by the headband 18, or alternatively by the helmet mounts, and thereby to the cushion 16A, 16B is not influencing the spring element 30A, 30B so as to design such a hearing protector 10 in a way that the properties such as noise attenuation and wearing comfort are not in conflict with each other. In a (Continued)

second aspect, the present disclosure relates to a method of retrofitting a hearing protector with a spring element 30A, 30B and a carrier 24A. 24B thereby providing the advantages and effects as laid out above.

19 Claims, 7 Drawing Sheets

(58) Field of Classification Search
CPC .............. H04R 1/1008; H04R 2460/15; H04R
5/0335; H04R 1/1016; H04R 1/1066;
H04R 1/1083
USPC ..................................................... 381/72, 74
See application file for complete search history.

(56) References Cited

U.S. PATENT DOCUMENTS

| | | | |
|---|---|---|---|
| 9,467,767 B2 * | 10/2016 | Chen ....................... | H04R 5/033 |
| 11,405,716 B2 * | 8/2022 | Freeman .............. | H04R 1/1058 |
| 2007/0094771 A1 | 5/2007 | Chen | |

FOREIGN PATENT DOCUMENTS

| | | | |
|---|---|---|---|
| FR | 1119367 | A | 6/1956 |
| GB | 779961 | A | 7/1957 |
| WO | 2006058319 | A1 | 6/2006 |
| WO | 2008070662 | A2 | 6/2008 |
| WO | 2016198707 | A1 | 12/2016 |
| WO | 2019104172 | A1 | 5/2019 |

* cited by examiner

HEARING PROTECTOR WITH SPRING ELEMENT AND A CARRIER

CROSS REFERENCE TO RELATED APPLICATIONS

This application is a national stage filing under 35 U.S.C. 371 of PCT/IB2022/052753, filed Mar. 25, 2022, which claims the benefit of EP Application Serial No. 21166716.7, filed Apr. 1, 2021, the disclosure of which is incorporated by reference in its/their entirety herein.

TECHNICAL FIELD

The present disclosure relates to a hearing protector with a spring element and a carrier.

BACKGROUND

Hearing protectors are typically used in noisy environments for protecting a wearer's hearing from noise at potentially harmful noise levels. Typically, hearing protectors have two earmuffs or caps which cover the ears of the wearer and which are connected to one another by a headband. Each cup further typically is formed by a rigid shell that is furnished with a noise attenuation material, for example a foamed material.

There is a general desire to make hearing protectors user-friendly, in particular to encourage persons that are in noisy environments for longer times to actually wear the protectors. While noise attenuation appears to be the most important property of a hearing protector, the wearing comfort of such a hearing protector also plays an important role. For example, a hearing protector with good noise attenuation properties may be uncomfortable to wear, particularly over an extended period of time like in a working environment during a full workday. So, even short interruptions of wearing may cause hearing impairment.

For example, hearing protectors are disclosed in WO2006/58319 or WO 2019/104172.

Sometimes the wearing compliance of a hearing protector is reduced if these are uncomfortable. Designing a hearing protector for good noise attenuation may lead to less comfort and vice versa, i. e. the noise attenuation and wearing comfort may influence each other. These properties of a hearing protector may act in different direction and may even conflict with each other. The noise attenuation properties of a hearing protector may depend on the pressure at which the earmuffs are pressing against the wearer's ear and head, respectively. Also, the mass of a hearing protector may be important for the noise attenuation. On the other hand, such properties may lead eventually to a lower wearing comfort of such hearing protectors as these might cause skin irritations due to the applied pressure. Also, such hearing protector might be heavy leading to discomfort.

Therefore, a need exists to design such a hearing protector in a way that the properties such as noise attenuation and wearing comfort are not in conflict with each other. There is a need for a hearing protector having a good wearing comfort while providing sufficient noise attenuation and vice versa.

SUMMARY

In a first aspect, the present disclosure relates to a hearing protector comprising two earmuffs each comprising a cushion with noise attenuation properties, a cup defining a hollow space and having noise attenuation properties, a carrier comprising at least one earmuff mount. The hearing protector further comprises a U-shaped headband for carrying the two earmuffs, alternatively two helmet mounts for carrying the two earmuffs at a protective helmet. The headband or the helmet mounts comprises two ends each having an earmuff attachment means for attaching the earmuffs to the headband. The cushion is connected to the carrier such that the cushion is carried by the carrier. As a result, the carrier may be mechanically decoupled, from a noise attenuation perspective, from the head of the user. The earmuff attachment means of the headband or of the helmet mounts engages the earmuff mount of the earmuffs such that the earmuffs are carried by the headband or by the helmet mounts. Each of the earmuffs comprises a spring element connecting the cup with the carrier. The carrier and the cushion form a first mass-spring system. The cup and the spring element form a second mass spring system. The spring element is configured and arranged such that the cup and the carrier are mechanically decoupled from each other. The advantage of such a hearing protector is that the hearing protector can be designed such that the aspects of comfort and noise attenuation can be addressed more independent of each other. It is noted that the cushion itself exhibits noise attenuation properties and contributes to the overall noise attenuation. This is because the mechanical interaction between the cup and the carrier is configurable independent of, i.e. separate from the cushion decoupling. The mass of the earmuff is being divided into two sub-masses by the spring element. The required force or pressure for proper sealing of the cushion to the wearer's ear and skin, respectively, can be designed independent of the mass-spring system of the cup and spring element. Also, the force or pressure applied to the carrier by the headband and thereby to the cushion is not influencing the spring element or the cup, neither static compression nor increase of stiffness. It is noted that the carrier typically provides for the force required to keep the earmuffs securely in place, i. e. covering or sealing the wearer's ears reliably, the result being two configurable resonances, i. e. cushion—carrier and spring element—cup, respectively. Also, the arrangement according to the present disclosure prevents that the spring element is compressed by the pressure applied to the carrier and provides for correct positioning and pressing of the cushion onto the wearer's skin required for noise attenuation and sealing.

Mechanical decoupling within the meaning of the present disclosure is understood as a frequency dependent change of the transmission of vibrations acting upon one part of the hearing protector to another part of the hearing protector. For example, vibration acting upon the cup will, dependent on frequency, have variable transmission to the carrier but also indirectly to the sound pressure level of the internal air cavity of the hearing protector. The mechanical decoupling may be affected at sound frequencies, e. g. 20-20 kHz but also important at lower frequencies and will be dominated by the resonances of the mass spring system. The system contains primarily two configurable resonances, i. e. cushion—carrier resonance and spring element—cup resonance respectively.

Noise attenuation within the meaning of the present disclosure is understood for an earmuff as consisting of noise attenuation and sound absorption. Noise attenuation represents that sound energy that is reflected away from the earmuff thus not reaching the user's eardrum and sound absorption, on the other hand, represents that sound energy is converted into heat. In other words, the reduction of noise impacting upon the wearer's ears relative to the noise level surrounding the wearer is achieved thereby. Noise attenuation may be passive through the construction of the hearing protector, e. g. by using sound insulating and/or sound absorbing materials, e. g. plastics, foams or foamed materials, on the one hand. The low frequency part of the sound attenuation is controlled by a system of masses, springs and dampers. In the present disclosure a second order system is suggested, i. e. two masses corresponding to carrier and cup and two springs corresponding to cushion and spring element. In comparison, a traditional earmuff would consist of a first order system where the mass corresponds to the combination of cup and carrier and the spring corresponding to the cushion. In addition, there are additional masses, dampers and springs, e. g. the internal air cavity of the cup and the headband etc., but to simplify the explanation, a first or second order system, respectively, is chosen. On the other hand, noise attenuation may also be active, where the hearing protector is configured with a so-called noise cancellation function. The noise cancellation function is typically provided by electronic components comprising a microphone for picking up sound from the exterior or interior of the earmuff and a loudspeaker for emitting sounds toward the wearer's ear within the earmuff and components for converting the sound picked up by the microphone into the sound emitted by the loudspeaker. Typically the conversion includes a phase shift between the sound picked up and the sound emitted so that the acoustic waves emitted by the loudspeaker compensate the sound penetrating into the earmuff toward a sound amplitude that is lower than the result of only the penetrating sound amplitude.

A cup within the meaning of the present disclosure is a part of the earmuff of the hearing protector and is typically formed by a substantially rigid shell. The cup defines a hollow space and is preferably shaped as a hemisphere or is substantially hemispheroid shaped. The cup has a closed end which—in use—faces away from the wearer's ear and a preferably ring-shaped edge facing—in use—towards the wearer's ear. The cup typically has noise attenuation properties due to its material, due to noise attenuation material therein and/or due to its shape and/or geometry. The cup may contain components of the hearing protector inside the hollow shape or attached to the cup at other locations such as outside or on top of the cup, e. g. electronic components such as loudspeakers, printed circuit boards, sensors, microphones or batteries. The cup typically represents a mass component within the meaning of the present disclosure, wherein the cup of the hearing protector usually has a dedicated mass. Typically, the higher the mass is, the better the noise attenuation is because a higher mass requires a higher sound energy to be moved. Thus, the resulting sound pressure level at ear will consequently be lower for a cup with higher mass. Ways to increase the mass include the selection of the shape and/or material of the cup and/or by adding additional weights to an existing cup of a certain weight.

A carrier within the meaning of the present disclosure is a part of the earmuff of the hearing protector. The carrier connects the cup of the earmuff with the cushion of the earmuff on the one hand and connects the earmuff with the headband on the other hand. The carrier comprises an earmuff mount for attaching the earmuff to the headband. The earmuff mount engages or connects to earmuff attachment means present at the headband. The carrier is adapted for carrying the cushion. The carrier may be ring-shaped and may be shaped and sized essentially in accordance to the shape and size of the cup and/or the cushion of the earmuff.

The carrier provides the required force or pressure for pressing on of the cushion onto the wearer's skin for sealing within accurate noise attenuation.

A cushion within the meaning of the present disclosure serves for sealing the space formed by the respective earmuff at a wearer's head when the hearing protector is worn by the wearer. Preferably the cushion is shaped to extend around a wearer's ear. So configured earmuffs are also referred to as "over ear" earmuffs in the field of hearing protectors and headphones. The cushion also mechanically decouples the carrier, such that it enables a stiffness and internal damping of the cushion spring as experienced by the mass, i. e. the carrier, which enables noise attenuation to the internal air cavity of the hearing protector. The cushion is preferably generally oval-shaped. Other shapes of cushions are conceivable, e. g. not extending around the wearer's ear, but to be placed on a wearer's ear thereby representing an "on-ear" earmuff. Preferably, the cushion comprises a soft, conformable and/or compressible material that conforms to the wearer's skin and/or ears such that a seal is achieved and only to a little extent noise can enter the earmuff interior. Typical suitable materials may comprise a foamed plastic material, for example Polyethylene (PE). The foamed material may include open- or closed-cell foams or materials rendered conformable. Further, the cushioning may comprise a sheath that encloses the soft material which helps to prevent sound transmission through the cushion. The sheath may be a plastic material selected from among polyvinyl-chloride (PVC) and thermoplastic polyurethane (TPU). Also, the cushion may be formed as a hollow shape defining a tube-like interior which may be gas or air filled to provide an air suspension. The skilled person will recognize other configurations for providing a cushioning that can adapt and seal to a wearer's head.

A headband within the meaning of the present disclosure is an elongated, band-like part connecting the two earmuffs of the hearing protector such that these can be placed on or over the ears of a wearer. The headband is typically U-shaped having two ends such that it fits over the wearer's head and such that it facilitates the positioning of the earmuffs on or over the wearer's ears. The headband applies a certain force or pressure to the earmuff and the cushion, respectively, to ensure accurate fit of the hearing protector. Typically, this force or pressure is in the range of 1 to 10 N as measured according to and as defined in European Standard EN 352-1, dated October 2002. Usually, the headband comprises attachment means for releasably or fixedly connecting the earmuffs thereto. Each earmuff of the hearing protector typically connects to one end of the headband. The headband may be replaced by helmet attachments means for the earmuffs in the case of using a helmet together with the earmuffs (see e. g. European product standard EN 352-3 dated October 2002). Thus, it is clear to the skilled person that—instead of the headband—helmet mounts may be arranged for carrying the earmuffs by or to connect the earmuff to a protective helmet. As a result, the earmuffs are finally carried by a protective helmet to which the helmet mounts may be attached.

A spring element within the meaning of the present disclosure is an element connecting the carrier to the cup of the hearing protector. The spring element facilitates the mechanical decoupling of the carrier from the cup of the earmuff such that it enables a stiffness and internal damping of the spring element as experienced by the mass, i. e. the cup and carrier. It is noted that the cushion of the hearing protector may typically—in addition to the spring element according to the present disclosure—also provide a spring function. The spring element facilitates the division of the mass of the earmuff into two masses thereby creating a second order mass spring system. The spring element may be ring-shaped and may comprise a mechanically damping material, e. g. an elastomeric material. It is noted that the material as well as the shape of the spring element contribute to the spring function of decoupling. The spring element may be configured as to compensate the noise attenuation to a comfort generating stiffness/damping change in the cushion.

In a further aspect, the present disclosure relates to a method of retrofitting a hearing protector with a spring element and a carrier. The hearing protector comprises two earmuffs each comprising a cushion with noise attenuation properties, a cup defining a hollow space and having noise attenuation properties, wherein the cups each comprise an earmuff mount. The hearing protector further comprises a U-shaped headband for carrying the two earmuffs, alternatively two helmet mounts for carrying the two earmuffs at a protective helmet. The headband or each of the helmet mounts comprises two ends each having an earmuff attachment means for attaching the earmuffs to the headband or to the helmet mounts. The cushion is connected to the cup such that the cushion is carried by the cup. The earmuff attachment means of the headband or of the helmet mounts engages the earmuff mount of the earmuffs such that the earmuffs are carried by the headband or by the helmet mounts. The method comprises the steps of disassembling the cushion from the cup: disassembling the earmuff from the headband or from the helmet mounts by disconnecting the earmuff mounts of the cup from the earmuff attachment means: assembling a spring element at the cup such that the spring element is carried by the cup: assembling a carrier at the spring element at a side thereof opposite to where the cup is assembled to such that the carrier is carried by the spring element: assembling the cushion to the carrier at a side thereof opposite to where the spring element is assembled to such that the cushion is carried by the carrier and assembling the earmuffs to the headband or to the helmet mounts. The advantages of such a method of retrofitting a hearing protector with a spring element and a carrier is that a conventional hearing protector is equipped such that the advantages and effects as laid out above for the hearing protector with the spring element and the carrier are achieved even for a hearing protector which originally did not have a spring element and a carrier.

In one embodiment, the spring element of the hearing protector is ring-shaped. Such a shape has the advantage that the shape is similar to other components of the hearing protector which are typically ring-shaped. Also, a ring shape allows for other components to be arranged therein without space limitations. Additionally, the spring element may also provide additional space for the pinna of the wearer's ear, i. e. helps to provide more design options.

In another embodiment, the spring element of the hearing protector comprises an elastomeric material. Such an elastomeric material may help to facilitate a mechanical decoupling provided by the spring element of the cup from the carrier with the cushion. Elastomeric materials typically exhibit good mechanical damping properties. Such materials may also be suitable to make a spring element with similar stiffness as the typical stiffness of the cushion. Preferably, the spring element of the hearing protector comprises a material selected from thermoplastic elastomers (TPE), thermoplastic polyurethane (TPU), synthetic rubber, a foam or foamed material, silicone, metals and/or combinations thereof. Such materials typically exhibit good mechanical damping properties. Such materials may also be suitable to use for a spring element with a similar stiffness compared to the cushion.

In yet a further embodiment, the spring element of the hearing protector is configured and arranged such that the resonance frequency of the cushion together with the carrier is similar to or higher than the resonance frequency of the cup together with the spring element. Such an arrangement has the advantage that good attenuation properties are achieved thereby, in particular, in the frequency range above the resonance frequencies.

In another embodiment, the cup of the hearing protector comprises a stiff material. Such a stiff material helps to provide for a robust and reliable design of the cup and the hearing protector, respectively. In particular, a stiff material helps to provide good shape maintaining properties of the cup. A stiff material is typically selected from ABS, PP, PA, PC, PVC and typically exhibits a stiffness of 1000 MPa to 3000 MPa. Alternatively, the cup may be made from a semi-stiff material, e. g. a high durometer elastomer or a composite of a rigid plastic and an elastomer. A stiff or semi-stiff material contributes to a cup providing for a specific resonance frequency, e. g. this can be used to control some resonance frequencies at high frequencies. However, these resonance frequencies are not the same resonances as controlled with the mass/spring system.

In one embodiment, the cup of the hearing protector comprises a moldable material, preferably an injection moldable material, wherein the material is preferably selected from Polypropylene, Polyethylene, Polystyrene, acrylonitrile-butadiene-styrene (ABS), Polyvinylchloride, metals or combinations thereof. The advantage of such moldable materials is that these can be easily manufactured with the desired shape required for the cup, in particular with the desired weight and thickness of the wall defining the hollow space. It is also conceivable to have composites of different materials, e. g. composites of metal with a polymeric material such as polyethylene or polypropylene. Such composites may be advantageous because metals in such compounds typically exhibit a good mechanical stability as well as electromagnetic interference protection properties. It is noted that this will also affect resonances at higher frequencies, however, not the same resonances as are affected with the mass/spring system.

In another embodiment, the cup of the hearing protector has a hemispheroid shape. Typically, the hemispherical shape has a closed end facing—in use—away from the wearer's ear and an open end facing—in use—towards the wearer's ear. The open end may be connected to the spring element of the hearing protector. It is noted that deviations from a perfect hemisphere, e. g. having an oval or elliptical cross-section in one or more planes, is also understood as hemispheroid shape within the meaning of the present disclosure. The advantage of such a hemispherical shape is that while a hollow space is defined, no sharp edges or corners are present.

In another embodiment, the cup of the hearing protector comprises an edge which is connected to or attached to the spring element, wherein the edge is preferably ring-shaped. Such an edge has the advantage that connection to the carrier is simplified thereby, in particular for a ring-shaped edge if connecting to a preferably ring-shaped carrier.

In a further embodiment, the carrier of the hearing protector is ring-shaped. Such a ring-shape of the carrier has the advantage that the shape is similar to other components of the hearing protector which are typically ring-shaped. Also, a ring-shape allows for other components to be arranged without space limitations, e. g. for components arranged within the earmuff which may protrude into the carrier.

In a preferred embodiment, the cushion and the carrier of the hearing protector are shaped and sized essentially in accordance with each other. Such a shape and size have the advantage that an easy reliable assembling is facilitated thereby. It is understood by the skilled person that this includes an arrangement where the cushion is slightly larger in cross-section than the carrier for the sake of comfort and/or to prevent the carrier from contacting the skin.

In another preferred embodiment, the spring and the cup of the hearing protector are shaped and sized essentially in accordance with each other. Such a shape and size have the advantage that an easy and reliable assembling is facilitated thereby.

In a further preferred embodiment, the cushion, the carrier, the spring element and the cup are shaped and sized essentially in accordance with each other. Such a shape and size have the advantage that an easy and reliable assembling is facilitated thereby.

In one embodiment, the carrier of the hearing protector comprises a stiff material. Such a stiff material helps to provide for a robust and reliable design of the carrier and the hearing protector, respectively. In particular, a stiff material helps to provide good shape maintaining properties of the carrier and helps with positioning of the earmuffs attached thereto. In particular, a stiff carrier may facilitate to apply the appropriate force or pressure to the earmuff for correct positioning and sealing of the cushions attached to the carrier. A stiff material is typically selected from ABS, PP, PA, PC, PVC and exhibits a stiffness of 1000 MPa to 3000 MPa. Alternatively, the carrier may be made from a semi-stiff material, e. g. a high durometer elastomer or a composite of a rigid plastic and an elastomer.

In another embodiment, the carrier of the hearing protector comprises a moldable material, preferably an injection moldable material, wherein the material is preferably selected from Polypropylene, Polyethylene, Polystyrene, acrylonitrile-butadiene-styrene (ABS), Polyvinylchloride, metals or combinations thereof. The advantage of such moldable materials is that these can be easily manufactured with the desired shape required for the carrier, in particular with the desired mechanical stability necessary for the correct positioning of the earmuffs attached to the carrier. It is also conceivable to have compounds of different materials, e. g. composites of metal with a polymeric material such as polyethylene or polypropylene. Such composites may be advantageous because metals in such composites typically exhibit a good mechanical stability as well as electromagnetic interference protection properties.

In yet another embodiment, the cup and/or the carrier of the hearing protector further comprises electronic components, wherein the electronic components preferably comprise a loudspeaker, a printed circuit board (PCB), a sensor, a microphone and/or a battery. The advantage of arranging components of the hearing protector within the cup and/or carrier is that a compact and robust design is achieved thereby. Also, impact of moisture, corrosion and/or mechanical damages of such components is avoided or reduced thereby. Components would not stick out of the hearing protector when arranged in this way. Also, additional masses of the components may be provided thereby, which helps to improve sound attenuation.

In a further embodiment, the carrier of the hearing protector further comprises an inner hemisphere connected to the carrier and arranged within the cup such that a gap is formed between the inner hemisphere and the cup. Such an inner hemisphere arranged within the cup of the hearing protector is advantageous as the hollow space as defined by the cup is divided into two sub-spaces thereby, wherein the double wall structure facilitates a good noise attenuation providing for an extra air cavity in addition to the hollow space as defined by the cup. Preferably, the gap between the inner hemisphere and the cup comprises a noise attenuation material, and/or electronic components. Such a material may, for example, include polyurethane foam, PVC foam or melamine foam. Such electronic components may, for example, include loudspeakers, microphones, sensors or other electronic components of an active noise cancellation unit, of an active communication unit and/or other components needed for the operation of a hearing protector. Such an arrangement is useful as it provides for a space-saving and compact arrangement of electronic components within the cup of the hearing protector. Also, the mass of the cap might be increased thereby. The arrangement of noise attenuation material is beneficial as it further supports the sound insulating and noise attenuation properties of the cup and the hearing protector, respectively. It is to be noted that maximizing the inner hemisphere may be beneficial as the sound pressure that is transmitted to the ear is essentially the sound energy per unit of volume in the inner cavity. The larger the volume, the lower the sound pressure is, i. e. sound energy per volume. On the other hand, the air cavity of the gap will affect the stiffness seen by the cup i.e. in combination to the stiffness of the spring element.

In yet a further embodiment, the cushion of the hearing protector is configured and arranged such that the cushion encapsulates the wearer's ear. Typically, the cushion is ring-shaped or ovally shaped in order to fit around the wearer's ear. Such an "over-ear" arrangement is beneficial as the cushion provides a good seal to the wearer's skin thereby which facilitates good noise cancelling properties of the hearing protector.

In still a further embodiment, the cushion of the hearing protector comprises a conformable and/or compressible material such that—in use—the cushion conforms to the skin of a wearer thereby forming a sound seal between the earmuff and the wearer's skin. A conformable and/or compressible material may compensate for an uneven and irregularly shaped surface as for example provided by the wearer's skin. Because of the deformation of the cushion material, a good contact and good comfort to the skin may be achieved. The advantage of such a conformable material for the cushion is that that it conforms to the wearer's skin and/or ears such that a good seal and comfort is achieved and no or only to a little extent noise can enter the earmuff interior. Preferably, the cushion comprises a foam or foamed material. The foam or foamed material may include an open cell foam or a closed cell foam. Such foams or foamed materials exhibit good conformability and/or compressibility and thus, these materials represent an easy and reliable way of providing a conformable and/or compressible material for the cushion.

In another embodiment, the cushion may comprise a combination of different materials. For example, the cushion may comprise a surface layer made from a rather robust material and may further comprise a rather soft, conformable and/or compressible material. The advantage of such a combination is that while providing for conformability and/or compressibility of the cushion, a reasonable robustness is provided at the same time. It is also conceivable that the cushion has an airtight outer layer which is filled with a fluid, e. g. air, which provides for the required conformability and/or compressibility. Such a solution may provide for an increased conformability and/or compressibility leading to increased comfort and/or sealing properties of the cushion. Other composites are conceivable as well, e. g. materials of different conformability and/or compressibility, such that a softer material is arranged—in use—towards the wearer's skin and a rather robust material is arranged—in use—away from the wearer's skin.

In still another embodiment, the hearing protector comprises an active noise cancellation unit and/or an active communication unit being arranged in or at one of the or both cups. An active noise cancellation unit or function as described above may provide for an increased noise attenuation property of the hearing protector. An active communication unit may provide for an increased functionality of the hearing protector, i. e. voice communication to other persons, entertainment audio and/or reproduction of ambient sound is enabled thereby. At the same time, such a unit may increase the weight of the cup leading to an increased mass of the cup within the meaning of a mass spring system. It is noted that some components of an active noise cancellation unit and/or the active communication unit may be placed outside of the cup, e. g. sensors which may be placed outside the cup.

In a certain embodiment, a loudspeaker, a sensor and/or an accelerometer is arranged in the gap between the inner hemisphere and the cup of the hearing protector. The advantage of such an arrangement is that the components placed in the gap, in particular a sensor, are protected by this position from an impulse in the inner cavity, e. g. when walking around while wearing the hearing protector.

In a certain embodiment, the hearing protector comprises an active noise cancellation unit which is configured and arranged to provide noise cancellation at a frequency region close to the resonance frequency of the hearing protector. The advantage of such an active noise cancellation unit is that the noise attenuation is compensated in a certain frequency region where the passive attenuation is lower. In one embodiment, the resonance frequencies of the cushion and carrier on the one hand, and the spring element and the cup on the other hand, of the hearing protector are selected such that these are adapted to specific noise environment. By such an arrangement, a customized noise attenuation of the hearing protector for a specific noise environment is achieved. It is also conceivable to configure and arrange the cushion and the carrier with their resonance frequencies together with the resonance frequency of the cup and the spring element such that a low frequency, a high frequency or flat sound attenuation characteristics is achieved. This is beneficial as the overall noise attenuation for different noise environments is improved thereby.

In another embodiment, the spring element of the hearing protector is configured and arranged such that the resonance frequency of the cushion together with the carrier when combined to the resonance frequency of the cup together with the spring element is adapted to the frequency characteristics of a specific noise environment. The advantage of such an arrangement is that a good noise attenuation is achieved and is even improved for specific noise environments.

The invention was described in various embodiments above. It is understood by a person skilled in the art that one of, several of or all the above-mentioned embodiments can be combined with each other.

The invention will now be described in more detail with reference to the following Figures exemplifying particular embodiments of the invention:

DETAILED DESCRIPTION OF THE FIGURES

Figure 1:
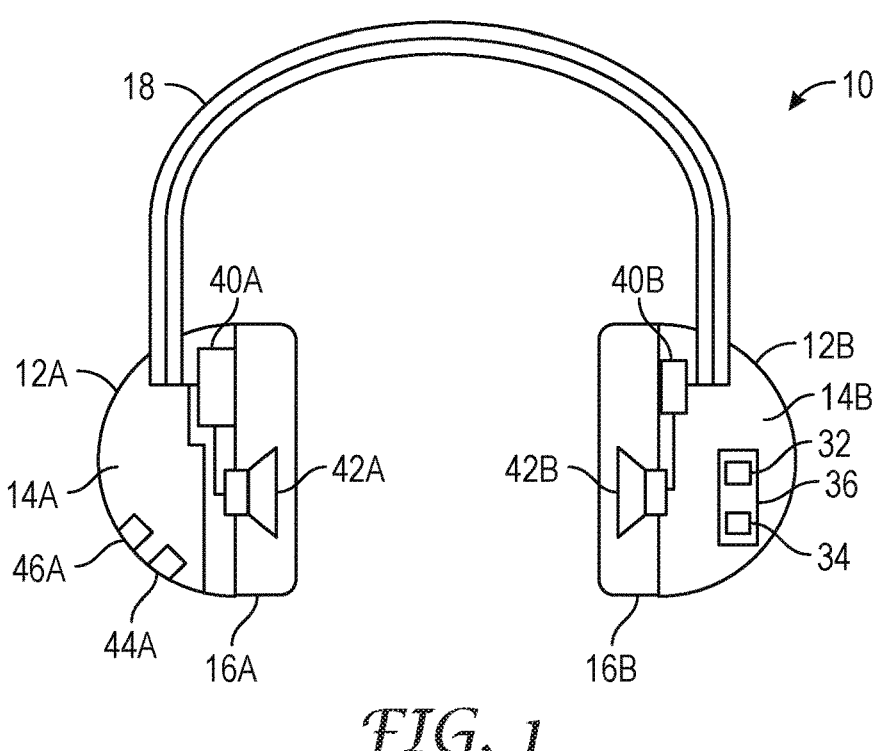
FIG. 1 is a schematic cross-sectional front view of the hearing protector of an embodiment according to the present disclosure.

FIG. 1 is a schematic cross-sectional view of the hearing protector 10 according to an embodiment of the present disclosure. The hearing protector 10 comprises two earmuffs 12A, 12B connected and carried by a headband 18. It is understood that instead of the headband 18, two helmet mounts (not shown here) may be present for carrying the earmuffs 12A, 12B. The earmuffs 12A, 12B each comprise an earmuff mount 20A, 20B through which each of the earmuffs 12A, 12B is attached to corresponding earmuff attachment means 22A, 22B of the headband 18. The earmuffs 12A, 12B are carried thereby by the headband 18. The earmuffs 12A, 12B each comprise a cup 14A, 14B defining a hollow space therein. In this hollow space, parts of components of the hearing protector 10 may be housed, for example printed circuit boards 36 with electronic components 32, 34 mounted thereon, sensors 44A or microphones 46A as shown in FIG. 1 for one of the earmuffs 12A, 12B. It is however conceivable that both earmuffs 12A, 12B comprise parts which are only illustrated for one earmuff 12A, 12B in FIG. 1. The earmuffs 12A, 12B may also comprise electronic components 40A, 40B, for example an amplifier 40A, 40B, for a loudspeaker 42A, 42B as shown in FIG. 1 as part of an active noise cancelling unit and/or as part of an active communication unit. The earmuffs 12A, 12B further each comprise a carrier 24A, 24B (not shown in FIG. 1, see FIG. 2). The earmuff mounts 20A, 20B are part of and extend from the carriers 24A, 24B. Each of the carriers 24A, 24B have a cushion 16A, 16B attached thereto. The cushion 16A, 16B comprises a soft, conformable and/or compressible material thereby sealing the earmuffs 12A, 12B to the skin of a wearer 100 (not shown in FIG. 1, see FIG. 2). The cushions 16A, 16B and the carriers 24A, 24B are preferably ring-shaped and are preferably shaped and sized essentially in accordance with each other such that an easy and reliable connection is achieved between these. The carriers 24A, 24B and/or the cushions 16A, 16B may comprise attachment means, e. g. adhesives or mechanical attachment means, which are not shown here, to facilitate the attachment to each other. The earmuffs 12A, 12B further each comprise a spring element 30A, 30B (not visible in FIG. 1, see FIG. 2), each of which are attached to each of the carriers 24A, 24B at a side opposite to the cushions 16A, 16B.

Figure 2:
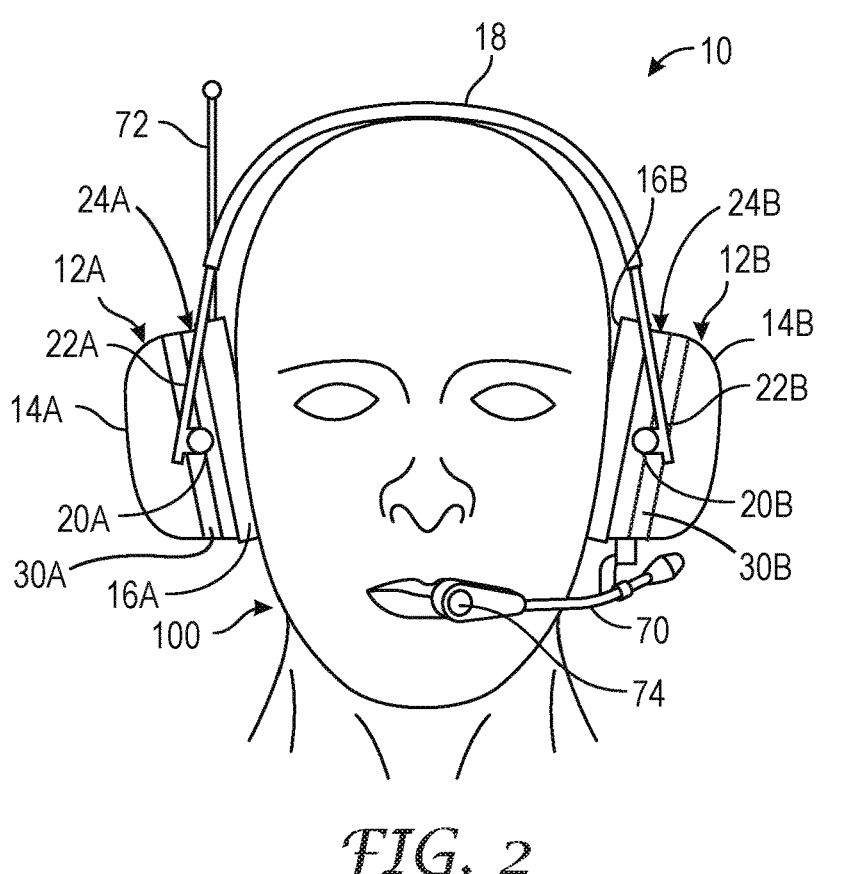
FIG. 2 is a schematic front view of an embodiment of the hearing protector according to the present disclosure worn by a wearer.

FIG. 2 shows in a schematic front view a similar embodiment of the hearing protector 10 as shown in FIG. 1 worn by a user or wearer 100. The hearing protector 10 is worn such that each of the earmuffs fit over an ear (not shown here) of the wearer. The hearing protector 10 as shown here comprises the same parts and components as shown in FIG. 1 and additionally a microphone 74 arranged at a microphone boom 70 extending from one of the earmuffs 12B as well as an antenna 72 extending from one of the earmuffs 12A. The microphone 70 and the antenna 72 may be part of an active communication unit of the hearing protector 10, although the antenna 72 may also transmit different signals other than voice signals, e. g. data signals from a sensor 46A as shown in FIG. 1. The hearing protector comprises two earmuffs 12A, 12B connected and carried by a headband 18. The earmuffs 12A, 12B each comprise an earmuff mount 20A, 20B through which each of the earmuffs 12A, 12B is attached to corresponding earmuff attachment means 22A, 22B of the headband 18. The earmuffs 12A, 12B are carried thereby by the headband 18. It is understood that instead of the headband 18, two helmet mounts (not shown here) may be present for carrying the earmuffs 12A, 12B. The earmuffs 12A, 12B each comprise a cup 14A, 14B defining a hollow space therein. In this hollow space, parts of components of the hearing protector 10 may be housed, for example printed circuit boards 36 with electronic components 32, 34 mounted thereon, sensors 44A or microphones 46A as shown in FIG. 1 for one of the earmuffs 12A, 12B. It is however conceivable that both earmuffs 12A, 12B comprise parts which are only illustrated for one earmuff 12A, 12B in FIG. 1. The earmuffs 12A, 12B may also comprise electronic components 40A, 40B, for example an amplifier 40A, 40B, for a loudspeaker 42A, 42B as shown in FIG. 1 as part of an active noise cancelling unit and/or as part of an active communication unit. The earmuffs 12A, 12B further each comprise a carrier 24A, 24B. The earmuff mounts 20A, 20B are part of and extend from the carriers 24A, 24B. Each of the carriers 24A, 24B have a cushion 16A, 16B attached thereto. The cushion 16A, 16B comprises a soft, conformable and/or compressible material thereby sealing the earmuffs 12A, 12B to the skin of a wearer 100. The cushions 16A, 16B and the carriers 24A, 24B are preferably ring-shaped and are preferably shaped and sized essentially in accordance with each other such that an easy and reliable connection is achieved between these. The carriers 24A, 24B and/or the cushions 16A, 16B may comprise attachment means, e. g. adhesives or mechanical attachment means, which are not shown here, to facilitate the attachment to each other. The earmuffs 12A, 12B further each comprise a spring element 30A, 30B, each of which are attached to each of the carriers 24A, 24B at a side opposite to the cushions 16A, 16B. As illustrated in FIG. 2, the earmuffs 12A, 12B each comprise a cup 14A, 14B, each of which are attached to the spring elements 30A, 30B at a side opposite to where the carriers 24A, 24B are attached to the spring elements 30A, 30B24A24B.

Figure 3:
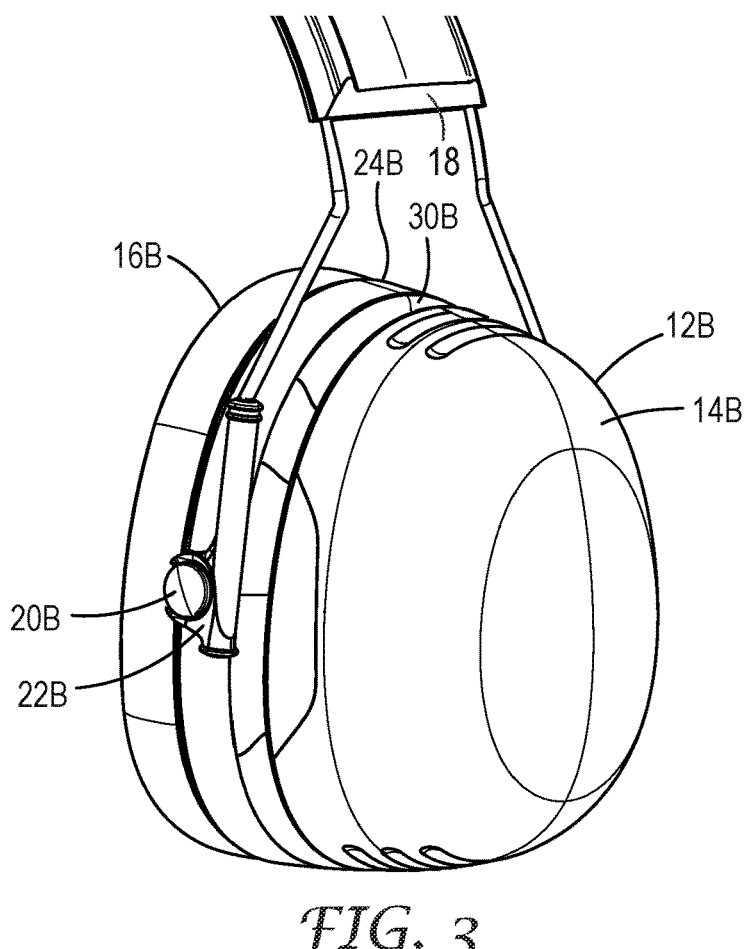
FIG. 3 is a perspective schematic view of an earmuff and part of the headband or a helmet mount of the hearing protector according to an embodiment of the present disclosure.

FIG. 3 shows in a perspective schematic view one of the earmuffs 12B of the hearing protector 10 as shown in FIG.

1 in greater detail. As can be seen, the earmuff 12B is attached with its earmuff mount 20B extending from the carrier 24B to the earmuff attachment means 22B of the headband 18 (only part of which is shown here). It is understood that instead of the headband 18, two helmet mounts (only a part of which is indicated here with 18) may be present for carrying the earmuffs 12A, 12B. As illustrated in FIG. 3, the earmuff 12B comprises a cup 14B attached to the spring element 30B at one side thereof. The carrier 24B is attached to the spring element 30B at a side opposite to where the cup 14B is attached. The cushion 16B is attached to the carrier 24B at a side opposite to where the spring element 30B is attached. Preferably, as shown in FIG. 3, the cushion 16B, the carrier 24B and the spring element 30B are ring-shaped. Also, the cup 14B of the earmuff 12B has—opposite to the close side—an open side with a preferably ring-shaped edge with which the cup 14B is attached to the above-mentioned preferably ring-shaped spring element 30B. It is understood that the constructional details as shown in FIG. 3 and as mentioned above, although only shown and mentioned for one of the earmuffs, may also be present on both earmuffs.

Figure 4:
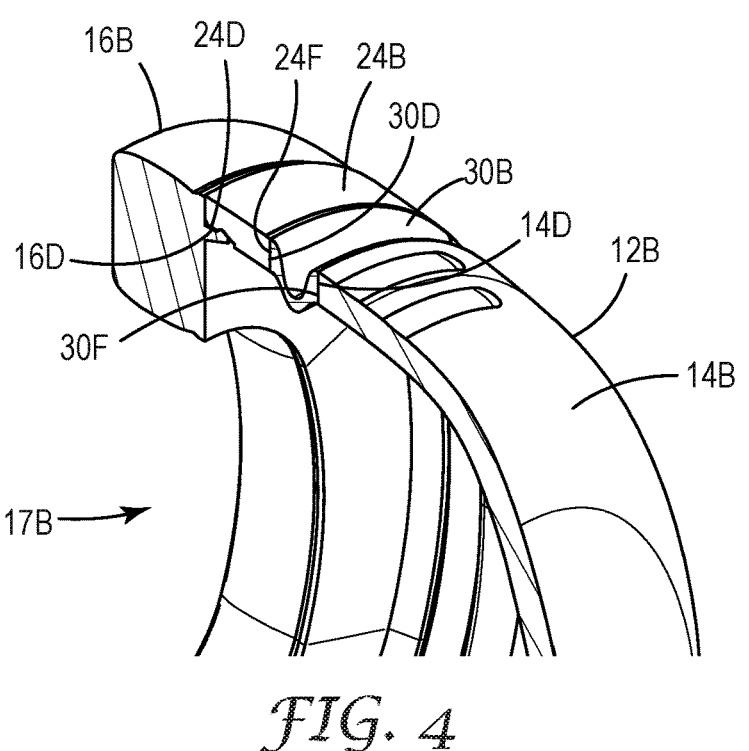
FIG. 4 is a perspective schematic cross-sectional view of the earmuff as shown in FIG. 3.

FIG. 4 shows in a perspective schematic cross-sectional view the earmuff 12B as shown in FIG. 3 in greater details. As can be seen, attachment means 16D, 24D are arranged to connect the cushion 16B with the carrier 24B at one side thereof. Furthermore, attachment means 24F, 30D are arranged to attach the spring element 30B to a side of the carrier 16B opposite to where the cushion 16B is attached. Attachment means 30F, 14D are arranged at a side of the spring element 30B opposite to where the carrier 16B is attached to facilitate attachment of the cup 14B to the spring element 30B. One of, some of or all the attachment means 16D, 24D, 24F, 30D, 30F, 14D may be formed as an adhesive or as a mechanical attachment means, e. g. a threaded portion, a bayonet or a snap fit connection. It is however also conceivable to form one of, some of or all the attachment means 16D, 24D, 24F, 30D, 30F, 14D as combined adhesive and mechanical attachment means. FIG. 4 furthermore shows an opening 17B in the preferably ring-shaped cushion 16B which facilitates encapsulation of the wearer's ear (not shown here) by the earmuff 12B. It is understood that the constructional details as shown in FIG. 4 and as mentioned above, although only shown and mentioned for one of the earmuffs, may also be present on both earmuffs.

Figures 5, 6:
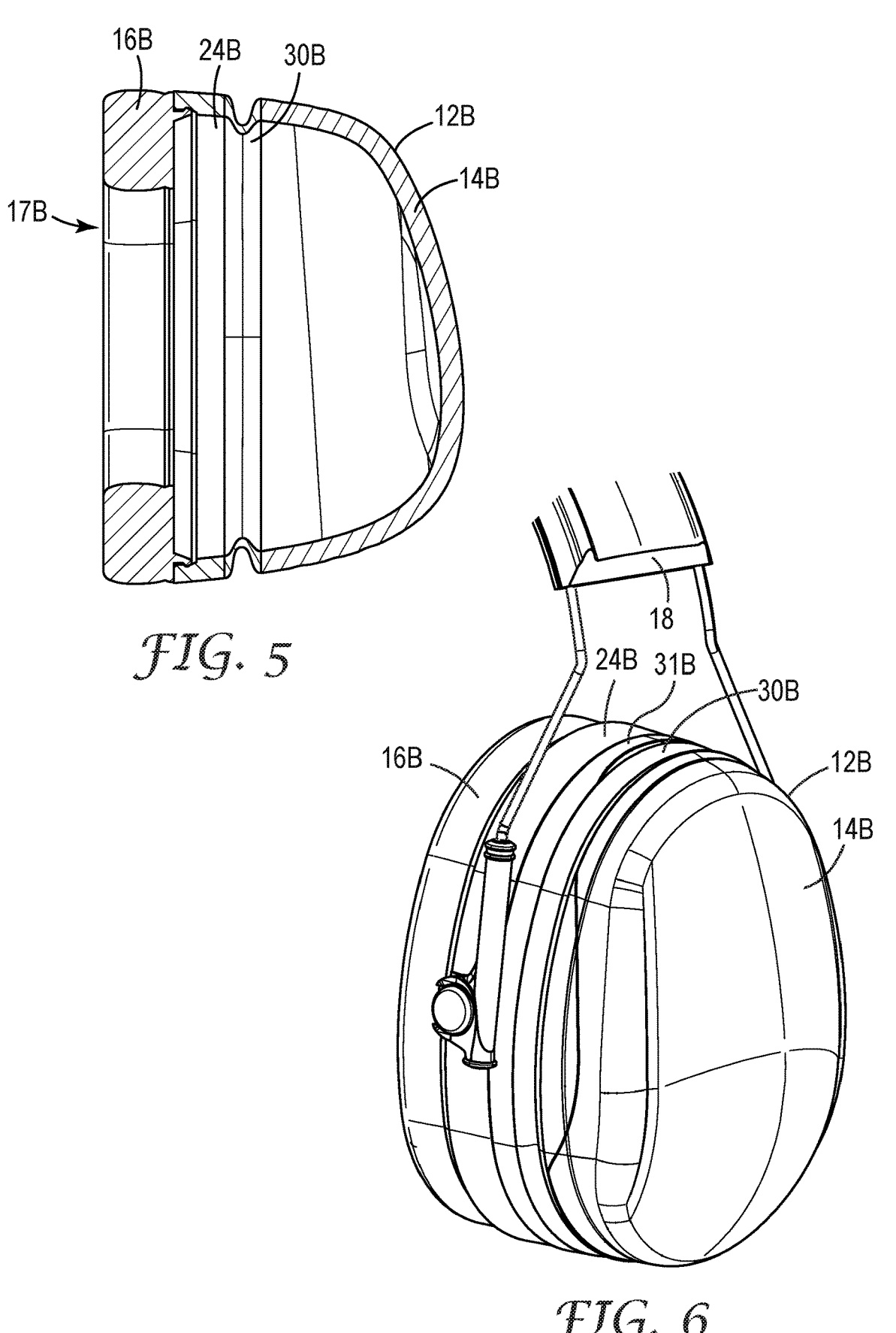
FIG. 5 is a schematic cross-sectional side view of the earmuff as shown in FIG. 3.
FIG. 6 is a perspective schematic view of an earmuff and part of the headband or a helmet mount of the hearing protector according to an embodiment of the present disclosure.

FIG. 5 shows in a schematic cross-sectional side view the earmuff 12B of the hearing protector 10 as shown in FIG. 1 in a more simplified way. As can be seen, the cushion 16B is attached to one side of the headband attachment means 24B. The spring element 30B is attached to the carrier 24B at a side opposite to where the cushion 16B is attached. Furthermore, the cup 14B is attached to the spring element 30B at a side opposite to where the carrier 24B is attached. Similar to FIG. 4, the cushion 16B comprises an opening 17B which facilitates encapsulation of the wearer's ear (not shown here) by the earmuff 12B. It is understood that the constructional details as shown in FIG. 5 and as mentioned above, although only shown and mentioned for one of the earmuffs, may also be present on both earmuffs.

FIG. 6 shows in a perspective schematic view the earmuff 12B of the hearing protector 10 according to an embodiment of the present disclosure. Different to the embodiment as previously described, the earmuff 12B further comprises an attachment ring 31B, which is only shown for one earmuff 12B, but it is understood that both earmuff 12A, 12B may comprise the attachment ring 31A, 31B. The attachment ring 31B is placed between the spring element 30B and the carrier 24B such that—different to the previously described embodiment—the attachment ring 31B is attached with one of its sides to one side of the carrier 24B, i. e. to the side opposite to where the cushion 16B is attached, and with its other side to one side of the spring element 30B, i. e. the side opposite to where the cup 14B is attached. FIG. 6 further shows part of the headband 18. It is understood that instead of the headband 18, two helmet mounts (only a part of which is indicated here with 18) may be present for carrying the earmuffs 12A, 12B.

Figure 7:
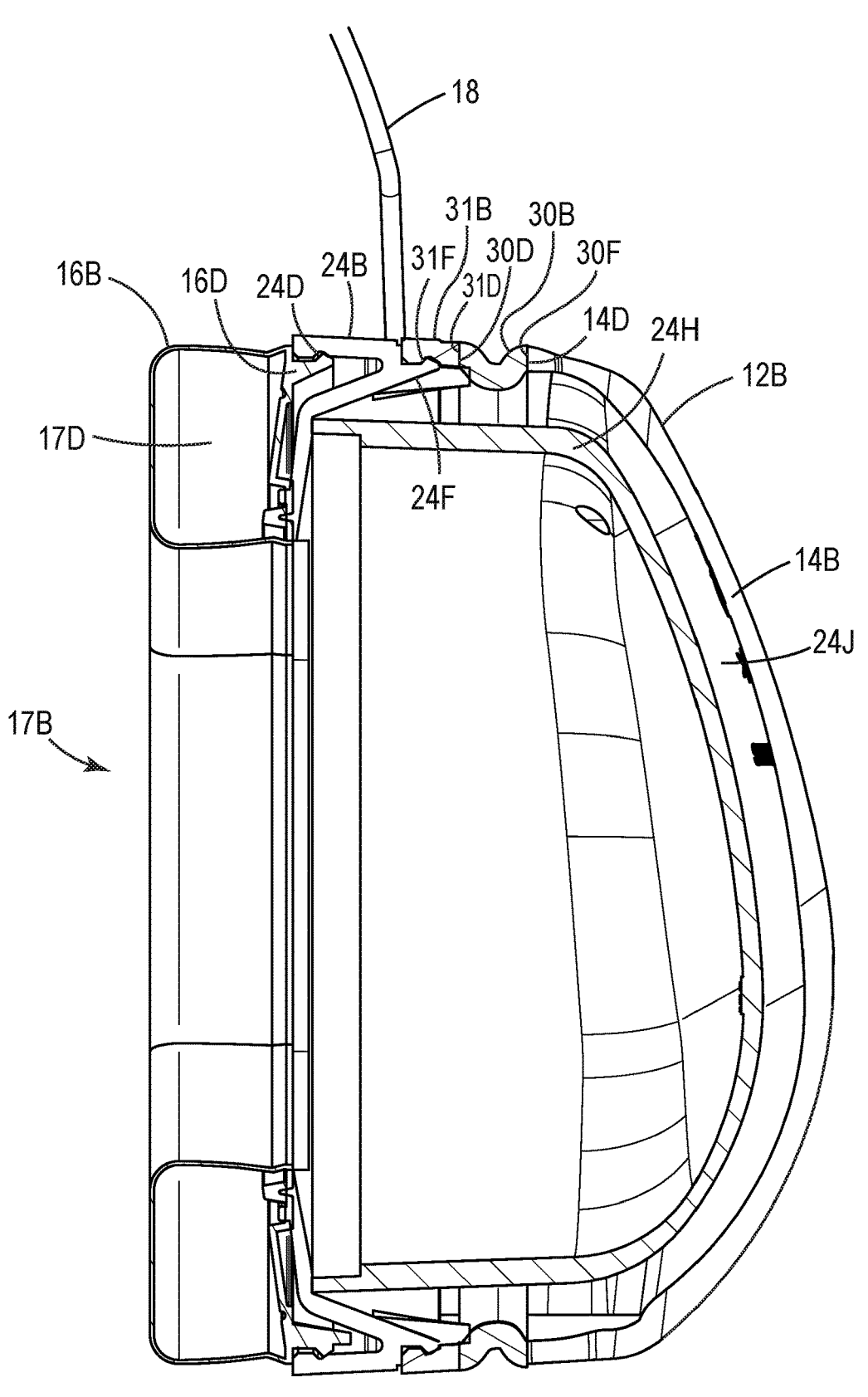
FIG. 7 is a schematic cross-sectional side view of the earmuff as shown in FIG. 6.

FIG. 7 shows in a schematic cross-sectional side view the earmuff 12B of the hearing protector 10 according to an embodiment of the present disclosure. In the embodiment shown, an inner hemisphere 24H is arranged as part of the carrier 24B. The inner hemisphere 24H may be an integral part of the carrier 24B or may be attached thereto with suitable adhesive or mechanical attachment means. The inner hemisphere 24H defines a hollow space within on the one hand and on the other hand defines—together with the cup 14B—a gap 24J between the inner and cup 24H, 24B. It is understood that the inner hemisphere 24H and the gap 24J, respectively, may be present on one or both earmuffs 12A, 12B. As described above, the inner hemisphere 24H divides the hollow space as defined by the cup 14B into two hollow spaces or sub-spaces, respectively, which leads to and helps to improve the noise attenuation using a double wall structure. This extra air cavity can also be used for an active system to position a loudspeaker and/or a microphone/sensor (not shown here). As can be seen, attachment means 16D, 24D are arranged to connect the cushion 16B with the carrier 24B at one side thereof. Furthermore, attachment means 24F, 30D are arranged to attach the spring element 30B to a side of the carrier 16B opposite to where the cushion 16B is attached thereto. Attachment means 30F, 14D are arranged at a side of the spring element 30B opposite to where the carrier 16B is attached to facilitate attachment of the cup 14B to the spring element 30B thereto. One of, some of or all the attachment means 16D, 24D, 24F, 30D, 30F, 14D may be formed as an adhesive or a mechanical attachment means, e. g. a threaded portion, a bayonet, or a snap fit connection. It is however also conceivable to form one of, some of or all the attachment means 16D, 24D, 24F, 30D, 30F, 14D as combined adhesive and mechanical attachment means. FIG. 7 also shows part of the headband 18 as shown in FIGS. 1 and 2 above. It is understood that instead of the headband 18, two helmet mounts (only part of which is indicated here with 18) may be present for carrying the earmuffs 12A, 12B. As mentioned above, FIG. 7 further shows—in addition to the arrangement of FIG. 4—an attachment ring 31B between the spring element 30B and the carrier 24B. Thus, as can be seen in FIG. 7, further attachment means 31D, 31F are present to attach the attachment ring 31B to the attachment means 24F of the carrier 24B on the one hand and to the attachment means 30D of the spring element 30B on the other hand. FIG. 7 furthermore shows an opening 17B in the preferably ring-shaped cushion 16B which facilitates encapsulation of the wearer's ear (not shown here) by the earmuff 12B. Additionally, FIG. 7 shows a cushion 16B which is of a hollow shape defining a tube-like interior 17D therein. For example, the interior 17D may be gas or air filled and provide a soft cushion 16B without the use of a foam or foamed material, but having an air suspension thereby achieving the conformability or compressibility required for the cushion 16B. It is to be noted, although the interior 17D, the attachment ring 31B and the inner hemisphere 24H with the gap 24J are shown together in FIG. 7, that only one of, some of or all these features are present in the earmuff 12B. It is also to be noted that one of, some of or all of these features are present in one or both earmuffs 12A, 12B.

Figure 8:
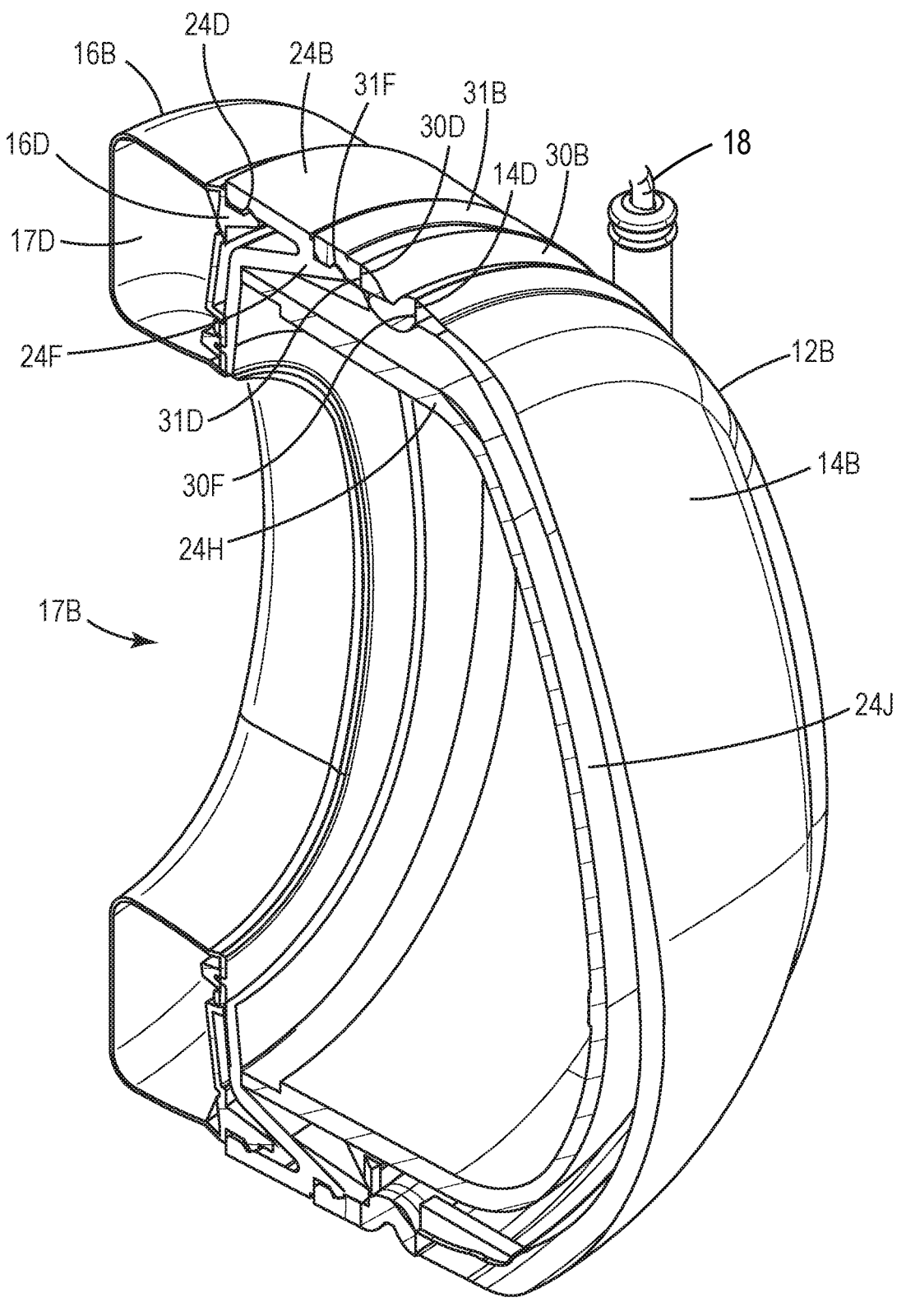
FIG. 8 is a perspective schematic cross-sectional view of the earmuff as shown in FIG. 6.

FIG. 8 shows in a perspective cross-sectional side view the earmuff 12B of the hearing protector 10 as shown in FIG. 7. In the embodiment shown, an inner hemisphere 24H is arranged as part of the carrier 24B. The inner hemisphere 24H may be an integral part of the carrier 24B or may be attached thereto with suitable adhesive or mechanical attachment means. The inner hemisphere 24H defines a hollow space within on the one hand and defines—together with the cup 14B a gap 24J therebetween. It is understood that the inner hemisphere 24H and the gap 24J, respectively, may be present on one or both earmuffs 12A, 12B. As described above, the inner hemisphere 24H divides the hollow space as defined by the cup 14B into two hollow spaces or sub-spaces, respectively, which leads to/helps to improve the noise attenuation using a double wall structure. This extra air cavity can also be used for an active system to position a loudspeaker and/or a microphone/sensor (not shown here). As can be seen, attachment means 16D, 24D are arranged to connect the cushion 16B with the carrier 24B at one side thereof. Furthermore, attachment means 24F, 30D are arranged to attach the spring element 30B to a side of the carrier 16B opposite to where the cushion 16B is attached thereto. Attachment means 30F, 14D are arranged at a side of the spring element 30B opposite to where the carrier 16B is attached to facilitate attachment of the cup 14B to the spring element 30B thereto. One of, some of or all of the attachment means 16D, 24D, 24F, 30D, 30F, 14D may be formed as an adhesive or a mechanical attachment means, e. g. a threaded portion, a bayonet or a snap fit connection. It is however also conceivable to form one of, some of or all the attachment means 16D, 24D, 24F, 30D, 30F, 14D as combined adhesive and mechanical attachment means. FIG. 8 also shows part of the headband 18 as shown in FIGS. 1 and 2 above. It is understood that instead of the headband 18, two helmet mounts (only part of which is indicated here with 18) may be present for carrying the earmuffs 12A, 12B. As mentioned above, FIG. 8 further shows—in addition to the arrangement of FIG. 4—an attachment ring 31B between the spring element 30B and the carrier 24B. Thus, as can be seen in FIG. 8, further attachment means 31D, 31F are present to attach the attachment ring 31B to the attachment means 24F of the carrier 24B on the one hand and to the attachment means 30D of the spring element 30B on the other hand. FIG. 8 furthermore shows an opening 17B in the preferably ring-shaped cushion 16B which facilitates encapsulation of the wearer's ear (not shown here) by the earmuff 12B. Additionally, FIG. 8 shows a cushion 16B which is of a hollow shape defining a tube-like interior 17D therein. For example, the interior 17D may be gas or air filled and provide a soft cushion 16B without the use of a foam or foamed material, but having an air suspension thereby achieving the conformability or compressibility required for the cushion 16B. It is to be noted, although the interior 17D, the attachment ring 31B and the inner hemisphere 24H with the gap 24J are shown together in FIG. 8, that only one or part of these features are present in the earmuff 12B. It is also to be noted that one of, some of or all these features are present in one or both earmuffs 12A, 12B.

Figure 9:
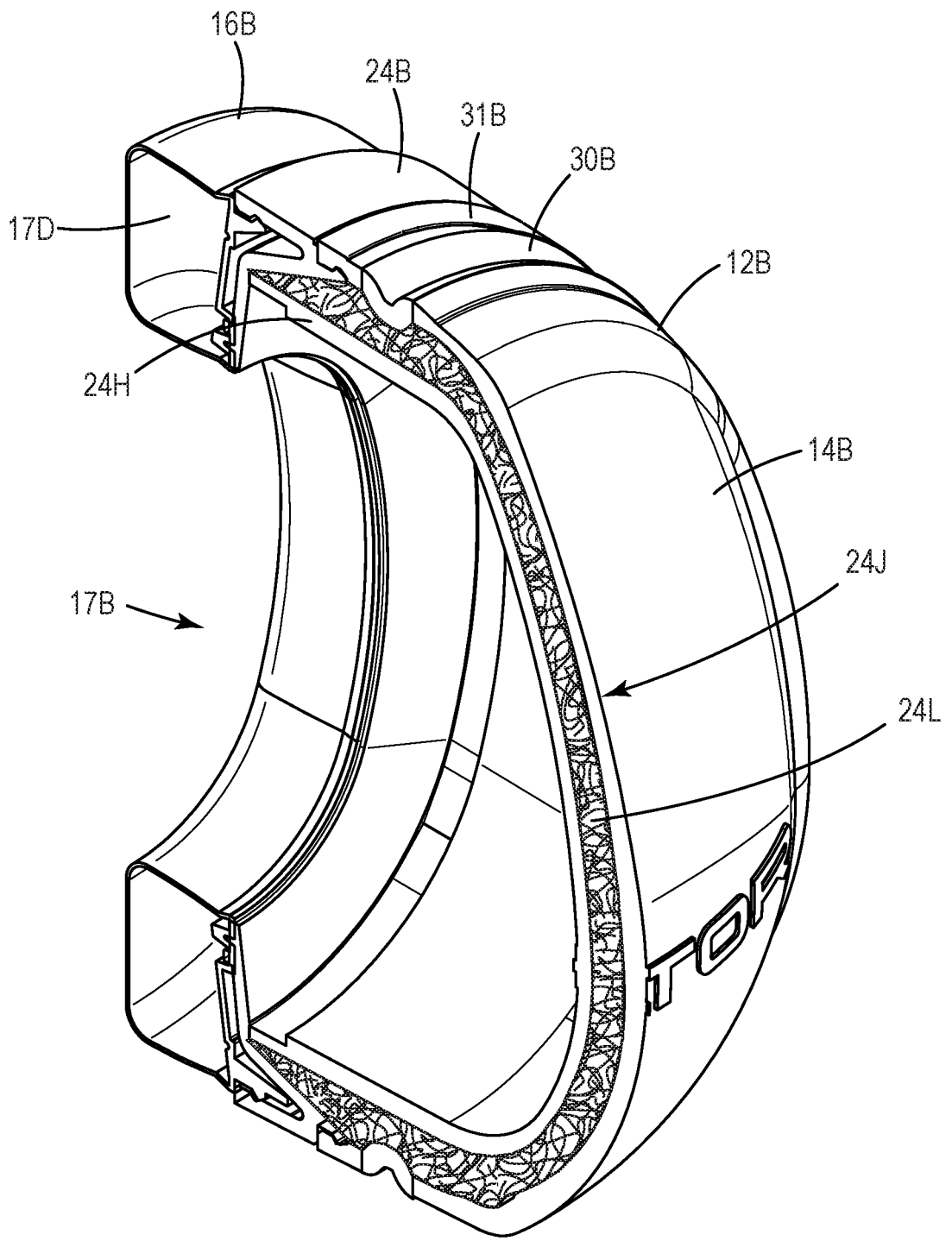
FIG. 9 is a perspective schematic cross-sectional view of an earmuff of the hearing protector according to an embodiment of the present disclosure.

FIG. 9 shows in a perspective schematic cross-sectional view the earmuff 12B of the hearing protector 10 as shown in FIGS. 7 and 8 in a more simplified way. As can be seen, the cushion 16B is attached to one side of the headband attachment means 24B. The spring element 30B is attached to the carrier 24B at a side opposite to where the cushion 16B is attached. Furthermore, the cup 14B is attached to the spring element 30B at a side opposite to where the carrier 24B is attached. Similar to FIG. 4, the cushion 16B comprises an opening 17B which facilitates encapsulation of the wearer's ear (not shown here) by the earmuff 12B. In addition to FIG. 4, FIG. 9 shows the attachment ring 31B arranged between the carrier 24B and the spring element 30B in the same way as described in FIGS. 7 and 8. Similar to FIGS. 7 and 8, the cushion 16B comprises an interior 17D formed therein which may be gas or air filled to provide for an air suspension of the cushion 16B. In addition, FIG. 9 shows that the gap 24J between the inner hemisphere 24H and the cup 14B is filled with a noise attenuation or vibration damping material as illustrated with 24L. A suitable material for filling includes e. g. polyurethane foams and mineral wool. It is to be noted, although the interior 17D, the attachment ring 31B and the inner hemisphere 24H with the gap 24J are shown together in FIG. 9, that only one of, some of or all these features are present in the earmuff 12B. It is also to be noted that one of, some of or all these features are present in one or both earmuffs 12A, 12B.

Figure 10:
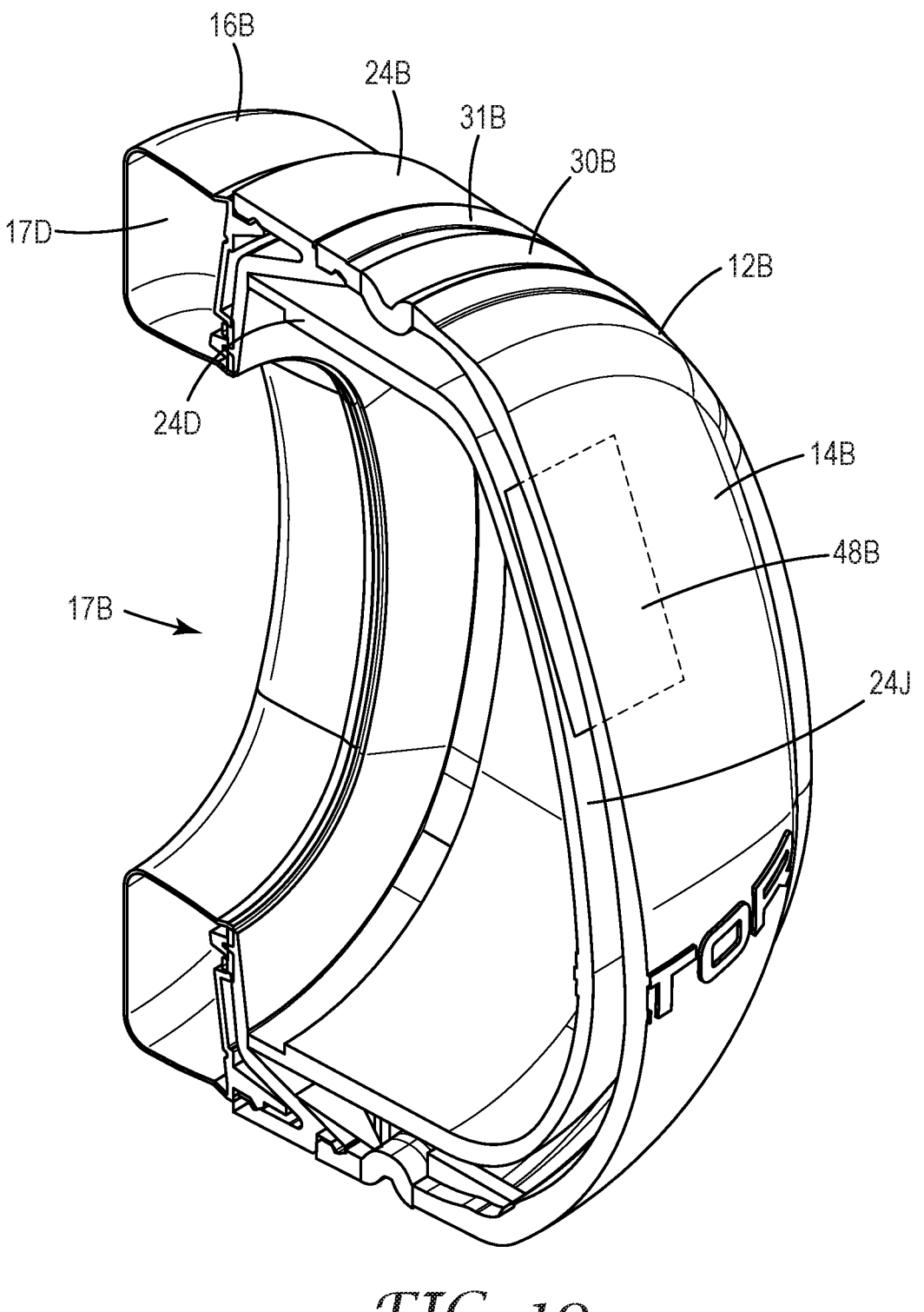
FIG. 10 is a perspective schematic cross-sectional view of an earmuff of the hearing protector according to an embodiment of the present disclosure.

FIG. 10 shows in a perspective schematic cross-sectional view the earmuff 12B of the hearing protector 10 as shown in FIG. 9, but without the noise attenuation material 24L arranged in the gap 24J between the inner hemisphere 24H and the cup 14B. Instead, electronic components including loudspeakers, microphones and sensors indicated with 48B are arranged in the gap 24J, for example parts of an active noise cancelling unit, of an active communication unit and/or other electronic components of the hearing protector 10, for example sensors, batteries, control units or the like. As can be seen, the cushion 16B is attached to one side of the headband attachment means 24B. The spring element 30B is attached to the carrier 24B at a side opposite to where the cushion 16B is attached. Furthermore, the cup 14B is attached to the spring element 30B at a side opposite to where the carrier 24B is attached. Similar to FIG. 4, the cushion 16B comprises an opening 17B which facilitates encapsulation of the wearer's ear (not shown here) by the earmuff 12B. In addition to FIG. 4, FIG. 10 shows the attachment ring 31B arranged between the carrier 24B and the spring element 30B in the same way as described in FIGS. 7 and 8. Similar to FIGS. 7 and 8, the cushion 16B comprises an interior 17D formed therein which may be gas or air filled to provide for an air suspension of the cushion 16B. It is to be noted, although the interior 17D, the attachment ring 31B and the inner hemisphere 24H with the gap 24J are shown together in FIG. 10, that only one or part of these features are present in the earmuff 12B. It is also to be noted that one of, some of or all these features are present in one or both earmuffs 12A, 12B.

The invention claimed is:

1. A hearing protector comprising:
two earmuffs each comprising:
    i. a cushion with noise attenuation properties;
    ii. a cup defining a hollow space and having noise attenuation properties, the cup comprising a ring-shaped edge; and
    iii. a carrier comprising at least one earmuff mount, wherein the carrier is ring-shaped and shaped and sized in accordance to the shape and size of the cup;
a U-shaped headband for carrying the two earmuffs, alternatively two helmet mounts for carrying the two earmuffs at a protective helmet, the headband or each of the helmet mounts comprising two ends, wherein each end comprises an earmuff attachment mechanism for attaching the earmuffs to the headband or to the helmet mounts;
wherein the cushion is connected to the carrier such that the cushion is carried by the carrier;
wherein the earmuff attachment mechanism of the headband or of the helmet mounts engages the earmuff mount of the earmuffs such that the earmuffs are carried by the headband or by the helmet mounts;
wherein each of the earmuffs comprises a spring element connecting the cup with the carrier on a side opposite the cushion, the ring-shaped edge of the cup is directly connected to or attached to the spring element; wherein the carrier and the cushion form a first mass-spring system and wherein the cup and the spring element form a second mass spring system; and
wherein the spring element is configured and arranged such that the cup and the carrier are mechanically decoupled from each other.

2. The hearing protector of claim 1, wherein the spring element is ring-shaped and circumferentially sized according to the ring-shaped edge of the cup.

3. The hearing protector of claim 1, wherein the spring element comprises an elastomeric material, preferably a material selected from thermoplastic elastomers (TPE), thermoplastic polyurethane (TPU), synthetic rubber, a foam or foamed material, silicone, metals and/or combinations thereof.

4. The hearing protector of claim 1, wherein the spring element is configured and arranged such that the resonance frequency of the cushion together with the carrier is similar to or higher than the resonance frequency of the cup together with the spring element.

5. The hearing protector of claim 1, wherein the cup comprises a moldable material, preferably an injection moldable material, wherein the material is preferably selected from Polypropylene, Polyethylene, Polystyrene, acrylonitrile-butadiene-styrene (ABS), Polyvinylchloride, metals or combinations thereof.

6. The hearing protector of claim 1, wherein the cup has a hemispheroid shape.

7. The hearing protector of claim 1, wherein the carrier comprises a moldable material, preferably an injection moldable material, wherein the material is preferably selected from Polypropylene, Polyethylene, Polystyrene, acrylonitrile-butadiene-styrene (ABS), Polyvinylchloride, metals or combinations thereof.

8. The hearing protector of claim 1, wherein the cup and/or the carrier further comprises electronic components, wherein the electronic components preferably comprise a loudspeaker, a printed circuit board (PCB) (36), a sensor, a microphone and/or a battery.

9. The hearing protector of claim 1, wherein the carrier further comprises an inner hemisphere connected to the carrier and arranged within the cup such that a gap is formed between the inner hemisphere and the cup, wherein the gap between the inner hemisphere and the cup preferably comprises a noise attenuation material and/or electronic components.

10. The hearing protector of claim 9, wherein a loudspeaker, a sensor and/or an accelerometer is arranged in the gap between the inner hemisphere and the cup.

11. The hearing protector of claim 1, further comprising an active noise cancellation unit and/or an active communication unit being arranged in or at one or both the cups.

12. The hearing protector of claim 1, wherein the spring element is configured and arranged such that the resonance frequency of the cushion together with the carrier when combined to the resonance frequency of the cup together with the spring element (30A, 30B) is adapted to the frequency characteristics of a specific noise environment.

13. The hearing protector of claim 1, wherein the cushion, the carrier, the spring element and the cup are shaped and sized essentially in accordance with each other.

14. The hearing protector of claim 1, wherein the carrier is ring-shaped.

15. The hearing protector of claim 1, wherein a force or pressure applied to the carrier by the headband and thereby to the cushion does not influence the spring element or the cup.

16. A method of retrofitting a hearing protector with a spring element and a carrier, the hearing protector comprising:

two earmuffs each comprising:
        a cushion with noise attenuation properties; and
        a cup defining a hollow space and having noise attenu-ation properties, the cup comprising a ring-shaped edge, wherein the cups each comprise an earmuff mount;
    a U-shaped headband for carrying the two earmuffs, alternatively two helmet mounts for carrying the two earmuffs at a protective helmet, the headband or each of the helmet mounts comprising two ends each having an earmuff attachment mechanism for attaching the earmuffs to the headband or to the helmet mounts;
    wherein the cushion is connected to the cup such that the cushion is carried by the cup;
    wherein the earmuff attachment mechanism of the headband or of the helmet mounts engages the earmuff mount of the earmuffs such that the earmuffs are carried by the headband or by the helmet mounts, the method comprising the steps of:

disassembling the cushion from the cup;
    disassembling the earmuff from the headband or from the helmet mounts by disconnecting the earmuff mounts of the cup from the earmuff attachment mechanism;
    assembling a spring element at the cup such that the spring element is carried by the ring-shaped edge of the cup;
    assembling a carrier at the spring element at a side thereof opposite to where the cup is assembled to such that the carrier is carried by the spring element;
    assembling the cushion to the carrier at a side thereof opposite to where the spring element is assembled to such that the cushion is carried by the carrier; and
    assembling the earmuffs to the headband or to the helmet mounts.

17. The method of claim 16, wherein the carrier is ring-shaped.

18. The method of claim 16, wherein the spring element is ring-shaped and circumferentially sized according to the ring-shaped edge of the cup.

19. The method of claim 16, wherein the spring element is ring-shaped and comprises a mechanically damping mate-rial.

\* \* \* \* \*